United States Patent [19]

Blancou et al.

[11] 4,452,852

[45] Jun. 5, 1984

[54] PROCESS FOR PREPARING POLYFLUORINATED ALCOHOLS

[76] Inventors: Hubert Blancou, Le Sylvie-Bâtiment A Rue Paul Rimbaud; Sylvie Benefice, Résidence le Prieuré, 31 bis, avenue St. Lazare, both of Montpellier, France, 34000; Auguste Commeyras, 6 Impasse des Ecoles, Clapiers, France, 34960

[21] Appl. No.: 461,995

[22] Filed: Jan. 28, 1983

[30] Foreign Application Priority Data

Feb. 23, 1982 [FR] France ............................... 82 02922

[51] Int. Cl.$^3$ ........................................... C07C 31/38
[52] U.S. Cl. .................................................... 568/842
[58] Field of Search ........................................ 568/842

[56] References Cited

U.S. PATENT DOCUMENTS 4,098,806  7/1978  Commeyras et al. ............... 568/842

Primary Examiner—Howard T. Mars
Attorney, Agent, or Firm—Pennie & Edmonds

[57] ABSTRACT

Process for preparing $R_FCH_2CH_2OH$ alcohols from $R_FCH_2CH_2I$ by reaction with a Zn/Cu metallic couple in the presence of a dissociation solvent having a water content of about 0.25 molar or less, oxidizing the resulting organometallic intermediate, and hydrolyzing the resulting product to form the corresponding perfluorinated alcohol. The perfluorinated alcohols are well known and are useful as intermediates for the production of valuable surface active agents as well as other useful materials.

6 Claims, No Drawings

PROCESS FOR PREPARING POLYFLUORINATED ALCOHOLS

FIELD OF THE INVENTION

This invention relates to a quantitative process of manufacture of polyfluorinated alcohols of the formula $$R_FCH_2CH_2OH$$

where $R_F$ is a perfluorinated radical. The alcohols are useful for the synthesis of chemical products with perfluorinated chains, usable, for example, as surface-active agents.

BACKGROUND OF THE INVENTION

Alcohols of the formula $R_FCH_2CH_2OH$ have been obtained by action of the $R_FCH_2CH_2I$ iodide on an amide in aqueous solution, as described in Japanese Pat. No. 37,520/1972, or by action of the same iodide on a fuming sulfuric acid, a process disclosed by U.S. Pat. No. 3,283,012. However, those processes result in medium yields, in the order of 71 and 84% respectively which is a major disadvantage taking into account the high price of the polyfluorinated materials used.

The reaction of $R_FI$ iodides on a metallic couple, such as Zn/Cu, in a dissociating solvent like dimethylsulfoxide (DMSO) or dimethylformamide (DMF) is also known. This heterogeneous reaction leads, through subsequent action of the intermediate product thus obtained on different substrates, to numerous functional perfluorinated compounds.

DISCLOSURE OF THE INVENTION

The present process relates to a process for the preparation of $R_FCH_2CH_2OH$ alcohols by the reaction of the $R_FCH_2CH_2I$ iodides on a Zn/Cu couple in a dissociating solvent, DMSO or DMF, and also in solvents such as alkyl and aryl carbonates and particularly alkyl and aryl phosphates while protecting the reaction from moisture. The intermediate product is oxidized in solution by a stream of oxygen and then hydrolyzed by a water/hydrochloric acid mixture in a medium buffered, for example, by a formic acid/sodium formate buffer.

The number of carbon atoms of the alkyl and aryl radical of the phosphates and carbonates can vary from 1 to 10, the only criterial being that alkyl and aryl phosphates and carbonates be dissociating solvents for the involved reaction. These types of carbonate and phosphate solvents are well known.

$R_F$ represents the radical $C_nF_{2n+1}$ where n is 1 to 20.

The perfluorinated alcohols are well known products and known to be useful as intermediates for the production of surface action agents and other valuable end products as disclosed, for example, in U.S. Pat. No. 3,283,012 incorporated herein by reference.

The alcoholic yield depends on the water content of the solvent. The latter can vary from 0 to 0.4 molar depending to some extent on the particular solvent employed.

The following examples illustrate the invention, without, however, limiting it.

EXAMPLE 1

The Zn/Cu metallic couple is prepared as follows:
To a solution of 0.2 g of copper acetate (0.001 mole) in 10 ml of acetic acid brought to boiling, 6.5 g of fine powdered zinc are added in small fractions. The couple thus prepared, washed three times with 40 ml of anhydrous DMSO, is ready for use.

One adds 0.05 mole of $C_4F_9CH_2CH_2I$ (18.7 g) drop by drop to the Zn/Cu couple dispersed in 30 ml of butyl phosphate containing 0.25% water. The butyl phosphate is dehydrated to a water content of less than 0.25 molar by prolonged stay on a molecular screen or on a drying resin.

The mixture is brought to a temperature of 80° C. and vigorously stirred for two hours. A stream of oxygen is then sent into the reaction mixture for 10 minutes and the mixture is then buffered by addition of a formic acid/sodium formate solution and hydrolyzed by a 20% aqueous hydrochloric acid solution.

After decanting, the organic part is extracted with ether and distilled under a pressure of 20 mm Hg.

One obtains 13.2 g of a product of 65° C. boiling point under 20 mm Hg, identified as $C_4F_9CH_2CH_2OH$, which corresponds to a 100% yield.

EXAMPLE 2

Example 1 is repeated but using 0.05 mole of $C_6F_{13}CH_2CH_2I$ (23.7 g). One obtains 18.2 g of a product of 87° C. boiling point under 20 mm Hg, which corresponds to a 100% yield of $C_6F_{13}CH_2CH_2OH$.

EXAMPLE 3

Example 1 is repeated but using 0.05 mole of $C_8F_{17}CH_2CH_2I$ (28.7 g). One obtains 23.2 g of a product of 115° C. boiling point under 20 mm Hg, which corresponds to a 100% yield of $C_8F_{17}CH_2CH_2OH$.

EXAMPLES 4 and 5

Examples 1 and 2 are repeated but using DMSO as the solvent containing 0.2 molar water. The yields are as follows:
with
$R_F=C_4F_9$; yield=10%
$R_F=C_6F_{13}$; yield=10%

EXAMPLES 6 and 7

Examples 1 and 2 are repeated but using DMF as the solvent containing 0.2 molar water. The yields are as follows:
with
$R_F=C_4F_9$; yield=25%
$R_F=C_6F_{13}$; yield=25%

EXAMPLE 8

Example 1 is repeated but using diethyl carbonate with 0.2 molar water as a solvent. The alcohol with $R_F=C_4F_9$ is obtained at a 30% yield.

We claim:
1. A process of preparing polyfluorinated alcohols of the formula $R_FCH_2CH_2OH$ where $R_F$ is a perfluoroalkyl radical containing 1 to 20 carbon atoms which comprises reacting $R_FCH_2CH_2I$ where $R_F$ is a perfluoroalkyl radical containing 1 to 20 carbon atoms with a Zn/Cu metallic couple in the presence of a dissociating solvent having a water content of about 0.4 molar or less to obtain an organometallic intermediate compound, and oxidizing the organometallic compound and hydrolyzing the oxidation product to produce the corresponding perfluorinated alcohol.

2. Process according to claim 1 in which the dissociating solvent is an alkyl or aryl phosphate with a water content of less than 0.25 molar.

3. Process according to claim 2 in which the dissociating solvent is a butyl phosphate.

4. Process according to claim 1 in which the dissociating solvent is an alkyl or aryl carbonate.

5. Process according to claim 1 in which the dissociating solvent is dimethylsulfoxide.

6. Process according to claim 1 in which the dissociating solvent is dimethylformamide.

* * * * *